United States Patent
Seth et al.

(10) Patent No.: US 11,534,623 B2
(45) Date of Patent: Dec. 27, 2022

(54) DETERMINING AT LEAST ONE FINAL TWO-DIMENSIONAL IMAGE FOR VISUALIZING AN OBJECT OF INTEREST IN A THREE DIMENSIONAL ULTRASOUND VOLUME

(71) Applicant: KONINKLIJKE PHILIPS N.V., Eindhoven (NL)

(72) Inventors: Subhendu Seth, Bangalore (IN); Pallavi Vajinepalli, Bangalore (IN); Achyuta Aich, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 620 days.

(21) Appl. No.: 16/496,505

(22) PCT Filed: Mar. 5, 2018

(86) PCT No.: PCT/EP2018/055364
§ 371 (c)(1),
(2) Date: Sep. 23, 2019

(87) PCT Pub. No.: WO2018/177691
PCT Pub. Date: Oct. 4, 2018

(65) Prior Publication Data
US 2020/0376295 A1 Dec. 3, 2020

(30) Foreign Application Priority Data
Mar. 30, 2017 (EP) .................................... 17163862

(51) Int. Cl.
*A61N 5/10* (2006.01)
*G06T 7/143* (2017.01)
*G06T 7/00* (2017.01)

(52) U.S. Cl.
CPC ......... *A61N 5/1007* (2013.01); *A61N 5/1048* (2013.01); *G06T 7/0012* (2013.01);
(Continued)

(58) Field of Classification Search
CPC .... G06V 40/19; G06V 40/161; G06V 10/454; G06V 10/82; G06T 7/0012; G06T 7/73; G06T 2200/04
See application file for complete search history.

(56) References Cited

U.S. PATENT DOCUMENTS 6,744,911 B1 6/2004 Avila
7,027,054 B1 * 4/2006 Cheiky ................. H04N 5/262
345/473

(Continued)

FOREIGN PATENT DOCUMENTS

WO 2015068099 A1 5/2015

OTHER PUBLICATIONS

Cheung et al; "Enhancement of Needle Visibility in Ultrasound Guided Percutaneous Procedures" Ultrasound in Med. & Biol., vol. 30, No. 5, pp. 617-624, 2004.
(Continued)

*Primary Examiner* — Yosef Kassa
(74) *Attorney, Agent, or Firm* — Sherry Austin (57) ABSTRACT

The present invention relates to a device (2) and a method (100) for determining at least one final two-dimensional image or slice for visualizing an object of interest in a three-dimensional ultrasound volume. The method (100) for determining at least one final two-dimensional image, the method comprises the steps: a) providing (101) a three-dimensional image of a body region of a patient body, wherein an applicator configured for fixating at least one radiation source is inserted into the body region; b) provid- (Continued)

ing (102) an initial direction, in particular by randomly determining the initial direction within the three-dimensional image; c) repeating (103) the following sequence of steps s1) to s4): s1) determining (104), via a processing unit, a set-direction within the three-dimensional image based on the initial direction for the first sequence or based on a probability map determined during a previous sequence; s2) extracting (105), via the processing unit, an image-set of two-dimensional images from the three-dimensional image, such that the two-dimensional images of the image-set are arranged coaxially and subsequently in the set-direction; s3) applying (106), via the processing unit, an applicator pre-trained classification method to each of the two-dimensional images of the image-set resulting in a probability score for each of the two-dimensional images of the image-set indicating a probability of the applicator being depicted, in particular fully depicted, in the respective two-dimensional image of the image-set in a cross-sectional view; and s4) determining (107), via the processing unit, a probability-map representing the probability scores of the two-dimensional images of the image-set with respect to the set-direction; wherein the method comprises the further step: d) determining (108), via a processing unit and after finishing the last sequence, the two-dimensional image associated with the highest probability score, in particular from the image-set determined during the last sequence, as the final two-dimensional image. The invention provides an efficient way to ensure that the ultrasound volume has the required clinical information by providing the necessary scan planes having the object of interest e.g. the applicator (6) in a three-dimensional ultrasound volume.

16 Claims, 5 Drawing Sheets

(52) U.S. Cl.
CPC .... *G06T 7/143* (2017.01); *G06T 2207/10136* (2013.01); *G06T 2207/20076* (2013.01); *G06T 2207/20081* (2013.01); *G06T 2207/20084* (2013.01); *G06T 2207/20108* (2013.01); *G06T 2207/30081* (2013.01); *G06T 2207/30096* (2013.01)

(56) References Cited

U.S. PATENT DOCUMENTS

| | | | |
|---|---|---|---|
| 7,742,623 B1* | 6/2010 | Moon | G06V 40/19 |
| | | | 382/103 |
| 8,123,691 B2 | 2/2012 | Mine | |
| 8,238,516 B2 | 8/2012 | Sakurai | |
| 8,379,794 B2 | 2/2013 | Poulsen | |
| 8,605,969 B2 | 12/2013 | Sofka | |
| 8,811,724 B2* | 8/2014 | Nielsen | G06T 7/0012 |
| | | | 382/128 |
| 8,885,882 B1* | 11/2014 | Yin | G06T 7/73 |
| | | | 382/103 |
| 9,129,054 B2* | 9/2015 | Nawana | A61B 34/20 |
| 9,311,527 B1* | 4/2016 | Yin | G06F 3/00 |
| 9,668,699 B2* | 6/2017 | Georgescu | G06T 7/0012 |
| 9,730,643 B2 | 8/2017 | Georgescu | |
| 10,143,398 B2 | 12/2018 | Altman | |
| 10,245,447 B2 | 4/2019 | Amthor | |
| 10,549,123 B2 | 2/2020 | Dehghan Marvast | |
| 10,631,829 B2 | 4/2020 | Dufour | |
| 10,667,786 B2 | 6/2020 | Peters | |
| 10,675,486 B2 | 6/2020 | Toimela | |
| 10,709,425 B2 | 7/2020 | Waechter-Stehle | |
| 2011/0243386 A1 | 10/2011 | Sofka et al. | |
| 2016/0157814 A1 | 6/2016 | Palanisamy | |
| 2016/0174902 A1 | 6/2016 | Georgescu et al. | |
| 2016/0317118 A1 | 11/2016 | Parthasarathy et al. | |
| 2018/0116635 A1 | 5/2018 | Dufour | |

OTHER PUBLICATIONS

Milletar et al. Hough-CNN: Deep Learning for Segmentation of Deep Brain Regions in MRI and Ultrasound Pattern Recognition, Feb. 2, 2016.
Search Report from PCT/EP2018/055364 dated Jun. 7, 2018.

* cited by examiner

DETERMINING AT LEAST ONE FINAL TWO-DIMENSIONAL IMAGE FOR VISUALIZING AN OBJECT OF INTEREST IN A THREE DIMENSIONAL ULTRASOUND VOLUME

CROSS REFERENCE TO RELATED APPLICATIONS

This application is a U.S. national phase application of International Application No. PCT/EP2018/055364 filed on Mar. 5, 2018, which claims the benefit of EP Application Serial No. 17163862.0 filed on Mar. 30, 2017 and is incorporated herein by reference.

FIELD OF THE INVENTION

The present invention relates to a device and a method for determining at least one final two-dimensional image or slice for visualizing an object of interest in a three-dimensional ultrasound volume.

BACKGROUND OF THE INVENTION

In brachytherapy, one or more radiation sources is placed inside the patient body in the treatment region comprising a tumor. Each radiation source emits ionizing radiation to treat the surrounding tissue with the main goal to destroy tumor cells included in this tissue. In one type of brachytherapy, which is usually called temporary brachytherapy, the radiation source is placed within the treatment region for a defined short time interval to apply the defined radiation dose particularly to the tumor cells. This type of brachytherapy calls for an efficient treatment of cervical cancer and other types of cancer, such as prostate/cervical cancer.

To place the radiation source within the treatment region, a so-called applicator is used. To prepare the radiation treatment, the applicator is inserted into the treatment region without including the radiation source. Once the applicator is correctly positioned, a dose calculation unit determines the dose distribution to be applied particularly based on the relative position between the applicator and the tumor and based on the anatomical configuration of the treatment region. Based on this dose distribution, an irradiation plan is then determined that specifies the positioning of the one or more radiation sources within the applicator and the treatment time such that the tumor cells are sufficiently treated and that sensitive tissue surrounding the tumor cells (also referred to as organs at risk) receives the lowest possible radiation dose. Thereupon, the radiation source is delivered into the applicator in accordance with the irradiation plan.

To help guide the placement of the applicator, images of the treatment region are used which are acquired using appropriate imaging modality. Moreover, the dose distribution and irradiation plan are determined based on an image acquired when the applicator is correctly positioned. In this regard, the irradiation plan is often determined based on several two-dimensional ultrasound images, which may be acquired from different (orthogonal) directions. In developing countries ultrasound proves to be a crucial modality of interest since access to other alternative modalities like computer tomography or magnetic resonance tomography are limited due to high cost burden.

Varied dimension of data is captured for better visualization of the object of interest to perform various clinical activities as e.g. in WO 2015/068099 A1 relating to an ultrasonic diagnostic imaging system and a method enabling the automatic acquisition of standard view planes of the heart in real time. In such context, three-dimensional ultrasound has been investigated for more than 20 years. With recent advancement in computation techniques and scanner technology, the acquisition of volumes with automatic three-dimensional probes has become less complicated and the quality of the images acquired by three-dimensional ultrasound has improved to become comparable to conventional ultrasound-B mode images. The acquisition of larger fields of view is one of the advantage of volumetric data. However, at the same time the scan plane must be clinically acceptable for ultrasonic measurement. Deviations from the above may require the clinicians to acquire multiple sets of ultrasound images to get the desired information thus affecting their clinical workflow.

SUMMARY OF THE INVENTION

There may be a need to have an efficient way to ensure that the ultrasound volume has the required clinical information by providing the necessary scan planes having the object of interest e.g. the applicator in a three-dimensional ultrasound volume. The object of the present invention is solved by the subject-matter of the independent claims; wherein further embodiments are incorporated in the dependent claims.

It should be noted that the following described aspects of the invention apply also for the apparatus, the system, the method, the computer program element and the computer readable medium.

According to a first aspect of the invention, a device for determining at least one final two-dimensional image is provided, wherein the device comprises: an input interface; and a processing unit; wherein the input interface is configured to receive a three-dimensional image of a body region of a patient body, wherein an applicator configured for fixating at least one radiation source is inserted into the body region; wherein the processing unit is configured to randomly determine an initial direction within the three-dimensional image, to receive a signal representing the initial direction via the input interface or to access a predefined direction as the initial direction; wherein the processing unit is configured to repeat the following sequence of steps s1) to s4): s1) determining a set-direction within the three-dimensional image based on the initial direction for the first sequence or based on a probability map determined during a previous sequence; s2) extracting an image-set of two-dimensional images from the three-dimensional image, such that the two-dimensional images of the image-set are arranged coaxially and subsequently in the set-direction; s3) applying an applicator pre-trained classification method to each of the two-dimensional images of the image-set resulting in a probability score for each of the two-dimensional images of the image-set indicating a probability of the applicator being depicted, in particular fully depicted, in the respective two-dimensional image of the image-set in a cross-sectional view; and s4) determining a probability-map representing the probability scores of the two-dimensional images of the image-set with respect to the set-direction; wherein processing unit is configured to determine, after finishing the last sequence, the two-dimensional image associated with the highest probability score, in particular from the image-set determined during the last sequence, as the final two-dimensional image.

The three-dimensional image may also be referred to a three-dimensional volume or a three-dimensional slice.

The basic idea of the invention is to take a known volumetric three-dimensional body region acquired by ultrasound measurements and automatically look for a slice comprising a sufficient illustration of the object of interest, i.e. the applicator. The first step the three-dimensional niche of the body region is sliced and one randomly determined direction. The slices are virtual slices of the three-dimensional body region. Furthermore, the slices may have constant distance from each other such that they are coaxial.

At least one of the slices comprises a part of the applicator image. When determining the probability map of the plurality of slices those slices comprising portions of the applicator get a high probability score. The probability scores are represented in a probability map of the two-dimensional images of the image set.

Based on the probability map a new set of slices is created in a new direction. That direction is determined based on the probability map analysis. For the new direction, a new probability map is determined. The sequence of determining probability maps is repeated until a probability map shows that the corresponding image set comprises a slice with a sufficiently good representation of the applicator.

The time a clinician spends having to browse through orthogonal planes to find the best image is reduced by the invention. Furthermore, it may be possible to create a two-dimensional view with an "in plane" view of the long axis of the applicator. According to an example, the final two-dimensional image is formed by the two-dimensional image associated with the highest probability score, in particular from the image-set determined during the last sequence.

Furthermore, in another example the processing unit is configured to perform step s2) such that the two-dimensional images of the image-set represent virtual slices of the body region. As an effect, the correspondence between the images and the virtual slices is provided.

In a certain example, the processing unit is configured to apply a Gaussian fit to the probability scores of the two-dimensional images of the image-set for determining the probability map. As an effect, the probability may will approximate a Gaussian curve representing the probability scores about the set-direction or number of two-dimensional images, respectively.

According to another example, step s4) comprises the sub-step: s4.1) finishing the repetition of the sequence, if the highest probability score of the probability scores of the two-dimensional images of the current image-set is higher than a predefined value, or if one two-dimensional image of the of the two-dimensional images of the current image-set entirely depicts the actuator in a cross-sectional view.

In a further example, step s4) comprises the sub-steps: s4.2) determining a standard deviation σ based on the probability map determined during the current sequence; and s4.3) finishing the repetition of the sequence, if a standard deviation σ determined during the at least one previous sequence represents a minimum standard deviation σ about all determined standard deviation σ. As an effect, the value of the standard deviation may provide the basis for a stopping criteria of the repetition of the sequence.

According to a further example, the processing unit is configured to perform step s1), if the set-direction is to be determined based on the probability map, with the following sub-steps: s1.1) determining a standard deviation σ based on the probability map; and s1.2) determining the set-direction based on the standard deviation σ. As an effect, determining the set-direction relates (except for the initial choice) to an iterative optimization algorithm.

According to a further exemplary embodiment, the device comprises the processing unit is configured to perform step s1), if the set-direction is to be determined based on the probability map, with the following sub-steps: s1.1) determining a gradient map based on the probability map; and s1.2) determining the set-direction based on the gradient map.

In another example, the applicator pre-trained classification method is an applicator pre-trained deep learning classification method.

According to a certain example, the applicator pre-trained classification method is an applicator pre-trained convolutional neuronal network classification method.

According to a second aspect of the present invention, an imaging system for determining at least one final two-dimensional image of a body region of a patient body is provided, comprising an applicator configured for fixating at least one radiation source is inserted into the body region, wherein the system comprises: an ultrasonic transducer; and a device according to one of the preceding claims; wherein the ultrasonic transducer is configured to acquire a plurality of two-dimensional ultrasonic images of the body region; wherein the system is configured to determine a three-dimensional image of the body region based on the plurality of two-dimensional ultrasonic images.

In a certain example, the processing is configured to perform step s2), such that a two-dimensional image is taken over from one of the plurality of the two-dimensional ultrasonic images, if the overtaken two-dimensional ultrasonic image fits into the respective image-set. As an effect, interpolation artefacts may be prevented or reduced.

According to a third aspect of the present invention, a method for determining at least one final two-dimensional image is provided, comprising the steps of:

a) providing a three-dimensional image of a body region of a patient body, wherein an applicator configured for fixating at least one radiation source is inserted into the body region;

b) providing an initial direction, in particular by randomly determining the initial direction within the three-dimensional image;

c) repeating the following sequence of steps s1) to s4):

s1) determining, via a processing unit, a set-direction within the three-dimensional image based on the initial direction for the first sequence or based on a probability map determined during a previous sequence;

s2) extracting, via the processing unit, an image-set of two-dimensional images from the three-dimensional image, such that the two-dimensional images of the image-set are arranged coaxially and subsequently in the set-direction;

s3) applying, via the processing unit, an applicator pre-trained classification method to each of the two-dimensional images of the image-set resulting in a probability score for each of the two-dimensional images of the image-set indicating a probability of the applicator being depicted, in particular fully depicted, in the respective two-dimensional image of the image-set in a cross-sectional view; and s4) determining, via the processing unit, a probability-map representing the probability scores of the two-dimensional images of the image-set with respect to the set-direction.

The method comprises the further step:

d) determining, via a processing unit and after finishing the last sequence, the two-dimensional image associated with the highest probability score, in particular from the image-set determined during the last sequence, as the final two-dimensional image.

With respect to the order of the steps it is noted that step a) is performed before step d). The step b) may have been computed or otherwise prepared beforehand. For step c), steps a) and b) must have been performed. Step d) is performed after step c.

According to a fourth aspect of the present invention, a computer program element is provided, which, when being executed by a processing unit is adapted to carry out the method described above.

According to a fifth aspect of the present invention, a computer readable medium having stored thereon a program element is provided, which, when being executed by a processing unit is adapted to carry out the method described above.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF THE EMBODIMENTS

Figure 3:
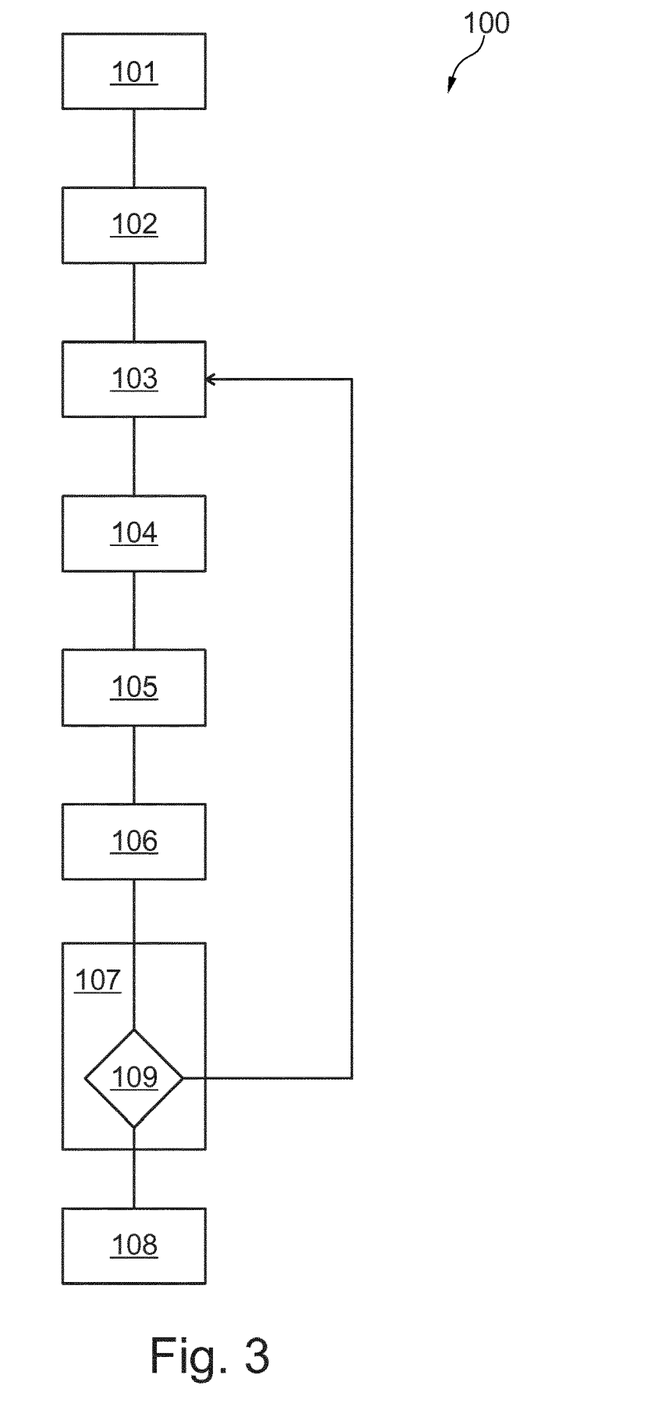
FIG. 3 shows a schematic view of an embodiment of the method.

Before further describing the imaging system and the device for determining at least one final two-dimensional image, examples of a method for determining at least one final two-dimensional image are described in further detail referring to FIG. 3.

FIG. 3 shows a method 100 for determining at least one final two-dimensional image. The method 100 comprises several steps.

In a first step 101 a three-dimensional image of the body region of the patient body is provided. An applicator is introduced in the patient body for fixating at least one radiation source in the body region. In an example, the three-dimensional image of the body region of the patient body is acquired by ultrasound measurements. Furthermore, the three-dimensional image of the body region of the patient body may be determined by two-dimensional images acquired by the ultrasound measurement.

In a second step 102 and initial direction within the three-dimensional image is provided. In an example the initial direction may be provided randomly. This means the method can provide any direction in the three-dimensional image of the body region of the patient.

In an example, the initial direction is determined as one of the predetermined Cartesian directions of the three-dimensional image.

In a further example, the initial direction may be provided via a signal representing the initial direction.

In an example, the initial direction may be provided via accessing a server or a memory device.

In a third step 103 a sequence of steps is started and repeated. In the following the steps of the sequence are described.

In a fourth step 104, a set-direction within the three-dimensional image based on the initial direction for the first sequence is determined via a processing unit. If previous sequences of the sequence have been performed the set-direction within the three-dimensional image is determined based on a probability map of at least one of the previous sequences. This means that when starting the sequence according to step 103 the first time the first sequence is started. For the first sequence the initial direction being acquired in step 102 represents the set-direction for the following steps. Starting with the second sequence, i.e. the first repetition of the sequence, the probability map of at least one of the previous sequences is used to determine the set-direction for the first repetition of the sequence.

In an example, the fourth step 104 may comprise the sub-steps of: identifying the set-direction of the three-dimensional image through a statistical analysis on the probability map which fetches a compact representation of the applicator.

In a fifth step 105, an image set of two dimensional images from the three-dimensional image is extracted via the processing unit. The extraction is performed such that the two-dimensional images of the image set are arranged coaxially and subsequently in the set-direction. This means that the three-dimensional image of the body region of the patient is sliced in a set of parallel planes along the set-direction and being orthogonal to the set-direction. Each plane thereby represents a two-dimensional image. The plurality of the planes represents the set of the two-dimensional images from the three-dimensional image.

In an example the two-dimensional images of the image set represent virtual slices of the body region. This means, that the three-dimensional image is virtually sliced to acquire the two-dimensional images. As an effect, the correspondence between the images and the virtual slices is provided.

In an example, the two-dimensional images represent the three-dimensional image in total.

As an effect, the three-dimensional image is divided into the two-dimensional images during the fifth step 105 of each sequence. Thus, for each evaluation of the respective probability scores, always the whole three-dimensional image is indirectly considered via the two-dimensional images.

In a sixth step 106, and applicator pre-trained classification method is applied to each of the two-dimensional images of the image set by a processing unit. The applicator pre-trained classification method determines a probability score for each of the two-dimensional images of the image set. The probability score being determined for a two-dimensional image indicates a probability of the applicator being depicted in that two-dimensional image. Since the three-dimensional image of the body region comprises an image of the applicator, the two-dimensional images may comprise at least a portion of the cross-sectional view of the applicator. The highest probability score is given if the cross-sectional view of the applicator shows the cross-section of the applicator along on the longitudinal axis of the applicator wherein the longitudinal axis is the longest axis inside the applicator. This means, if a two-dimensional image comprises the longitudinal axis of the applicator, the full cross-section of that applicator is fully shown in that two-dimensional image.

The lowest probability score may be assigned if the applicator pre-trained classification method does not find any portion of the image of the applicator in the corresponding two-dimensional image.

In an example, the applicator pre-trained classification method is an applicator pre-trained deep learning classification method.

In another example, the applicator pre-trained classification method is an applicator pre-trained convolution of neuronal network location method.

In a further example the applicator pre-trained classification method is pre-trained with a google net architecture or with a hyper-parameter fine-tuning In a seventh step 107, the processing unit determines a probability map representing the probability scores of the two-dimensional images of the image set with respect to the set-direction. This means, that the probability scores are mapped in a probability map wherein the x-axis of the map represents the position of the two-dimensional image of that probability score and the y-axis represents the probability score being determined by the applicator pre-trained classification method for that two-dimensional image.

In an example, a Gaussian fit is performed on the probability scores of the two-dimensional images of the image set for determining the probability map. As an effect, the probability will approximate a Gaussian curve representing the probability scores about the set-direction or number of two-dimensional images, respectively.

In an exemplary embodiment, the seventh step 107 comprises a sub-step 109. In the sub-step 109, the repetition of the sequence is finished if a high probability score of probability scores of the two-dimensional images of the current image set is higher than a predefined value. Alternatively, the repetition of the sequences is finished if one two-dimensional image of the two-dimensional images of the current image that entirely depicts the actuator in a cross-sectional view. This means, that if a slice of the three-dimensional image comprises the longitudinal axis of the actuator or is at least parallel to the longitudinal axis of the actuator and comprises a cross-sectional view of the actuator the sequence is finished. Alternatively, if the angle between the longitudinal axis and the slice of the three-dimensional image is below a certain threshold such that the probability score of one of the slices exceeds a predefined threshold value, the sequence will be finished, too.

In an example, the predefined value may be chosen or predefined, such that it can be assumed that the two-dimensional image corresponding to the respective highest value at least almost entirely depicts the actuator in a cross-sectional view.

Figure 4:
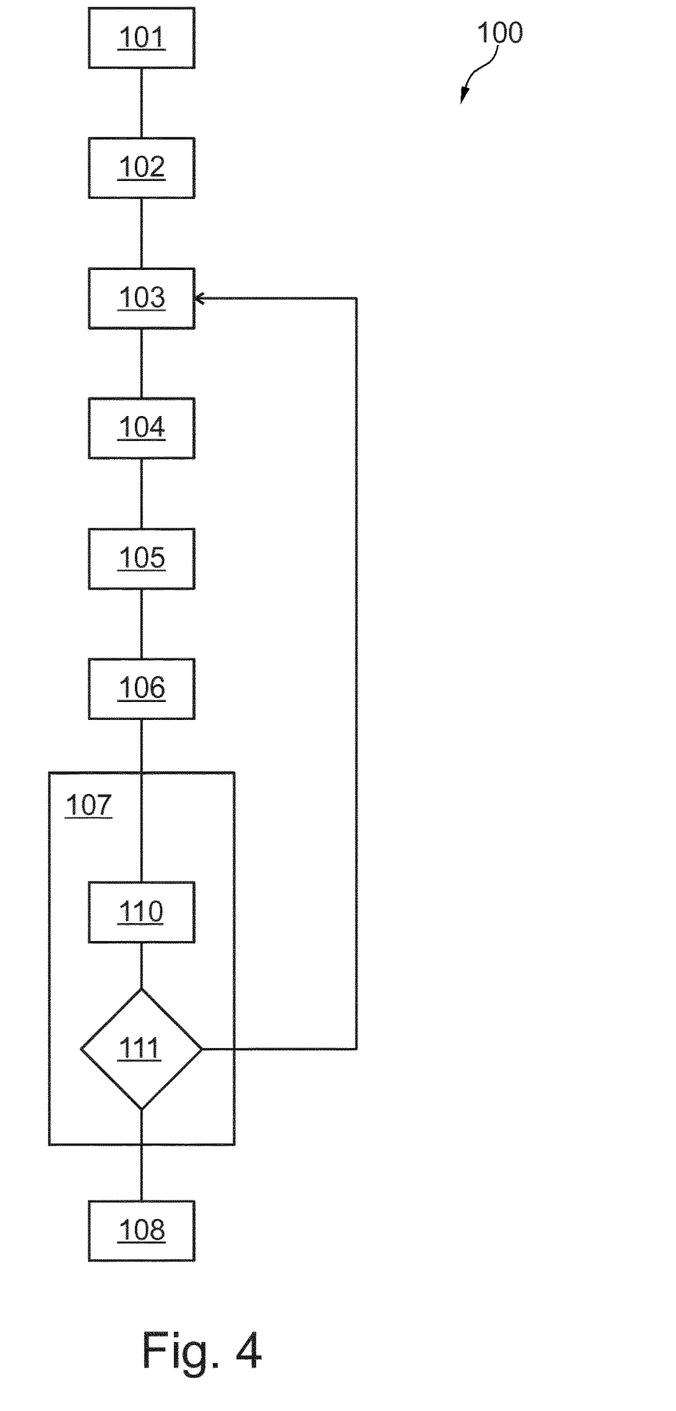
FIG. 4 shows a schematic view of another embodiment of the method.

In a further exemplary embodiment being shown in FIG. 4, the seventh step 107 comprises further sub-steps 110 and 111.

In a step 110, a standard deviation σ based on the probability map is determined using the current sequence. This means, that the maximum value of the probability scores of a probability map of the current sequence is determined. Then the standard deviation σ of the plurality of probability scores from that maximum value is determined.

In an eighth step 111 the repetition of the sequences is finished if the determined standard deviation σ represents a minimum standard deviation σ about all determined standard deviations σ. The determined standard deviation σ of the current sequence is therefore compared to the determined standard deviation σ of the previous sequences. If one of the previous sequences comprises the minimum standard deviation σ about all sequences, i.e. if the standard deviation σ of the current sequence is higher than one of the previous sequences, the repetition of the sequence is stopped.

As an effect, the value of the standard deviation may provide the basis for a stopping criteria of the repetition of the sequence.

The steps 104 to 107 are part of the repeated sequence of the third step 103.

In an example, the sequence may be repeated several times. At each sequence, an improved set-direction may be determined, along which a set of two-dimensional-images are extracted from (the same) three-dimensional-image. The probability associated with each image may provide the information about a compactness of an indication of the applicator within the respective two-dimensional-image. A probability may be determined based on the probabilities of the two-dimensional-image. At the next sequence, this probability map may be considered, to determine a new set-direction. Thus, an optimization of the set-direction may be achieved. As an effect, the images acquired along an optimized or best set-direction, respectively, may comprise at least one two-dimensional-image, which indicate a (very) compact representation of the applicator. Thus, the at least one image may illustrate a cross-sectional view of the full applicator.

In the step 108, the processing unit determines the final two-dimensional image from the two-dimensional image associated with the highest probability score after finishing the last sequence.

In an example, the highest probability score is determined from the image set of the last sequence. This means that the processing unit assigns the two-dimensional image having the highest probability score from the last sequence as final two-dimensional image. This means, that the final two-dimensional image comprises the best cross-sectional view of the applicator being found by the method. The final two-dimensional image may be presented to the staff to indicate the position of the applicator in the body region of the patient.

In an example, the probability may represent a Gaussian probability map, wherein the standard deviation decreases from sequence to sequence. Thus, the probability map determined during the last sequence may comprise the two-dimensional-image for which the highest probability score is determined.

In an example, determining the set-direction based on the probability may relate to an application of an iterative optimization algorithm, in particular a gradient descent algorithm.

Furthermore, in an example, the final two-dimensional image may be formed by the two-dimensional image associated with highest probability score of image set.

Figure 5A:
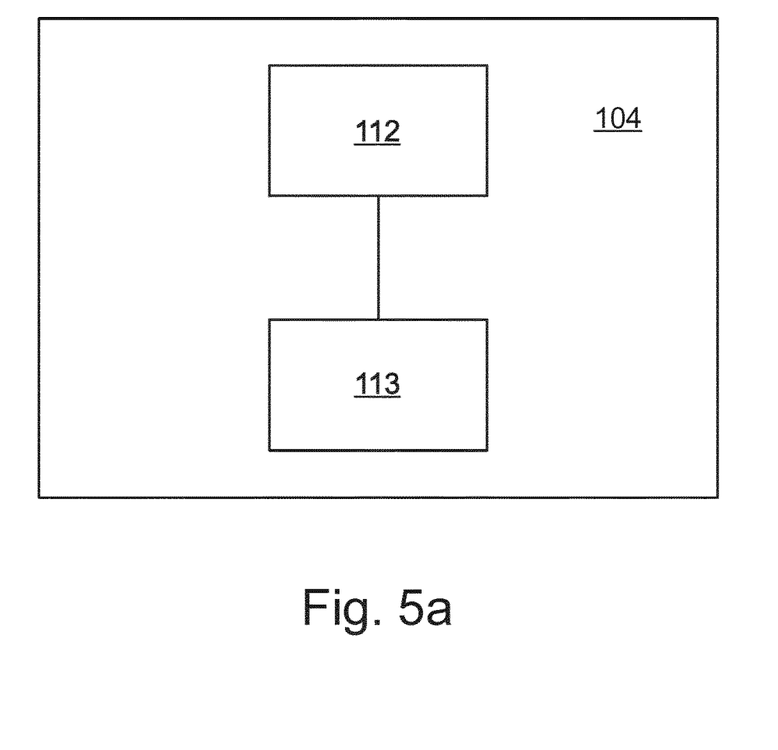
FIG. 5A, B show embodiments of step s1).

FIG. 5a shows an exemplary embodiment of the fourth step 104. In that embodiment step 104 comprises the sub-steps 112 and 113. Steps 112 and 113 are performed only, if the set-direction is to be determined based on the probability map of at least one previous sequence.

In step 112, the standard deviation σ based on the probability map is determined.

In step 113, the set-direction is determined based on the standard deviation σ. If the standard deviation σ is high the set-direction of the current sequence will deviate from the set-direction of the previous sequence by a high amount, i.e. the angle between the set-direction of the current sequence and the set-direction of the previous sequence will be high. If standard deviation σ is very low, the set-direction of the current sequence will not deviate much from the set-direction of the previous sequence, i.e. the angle between the set-direction of the current sequence and the set-direction of the previous sequence will be small.

Figure 5B:
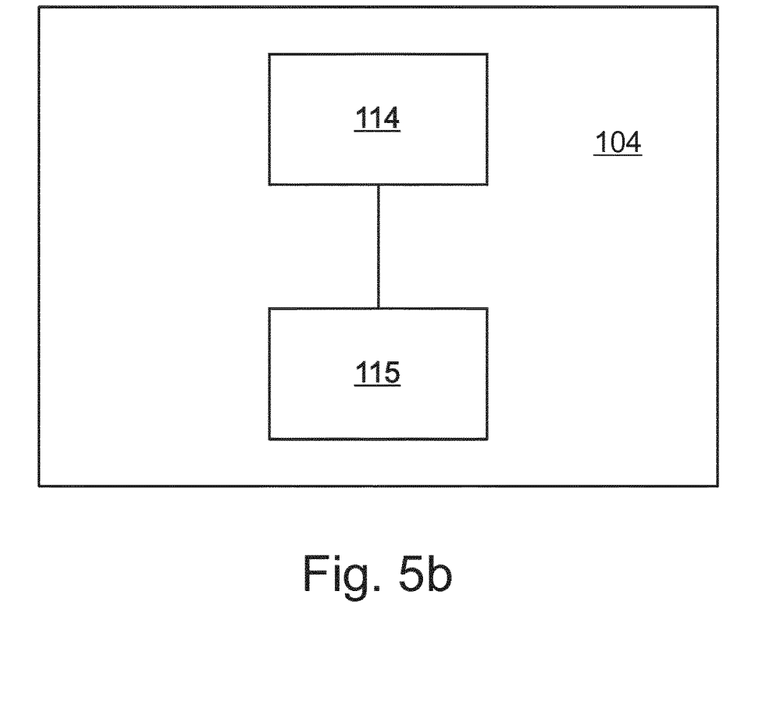

FIG. 5b shows another embodiment of step 104. In that embodiment step 104 comprises sub-steps 114 and 115. Steps 114 and 115 are performed only if the set-direction is to be determined based on the probability map.

In step 114 a gradient map based on the probability map is determined. This means that the gradient values between the probability scores of adjacent two-dimensional images of the three-dimensional image are determined. The gradient map comprises the plurality of determined gradient values and maps them to the position of the corresponding two-dimensional image in the three-dimensional image.

In step 115, the set-direction is determined based on the gradient map. This means, if high gradient values indicating a big change between the probability scores of adjacent two-dimensional images are distributed in a big region along the set-direction, the set-direction of the current sequence will deviate from the set-direction of the previous sequence by a high amount, i.e. the angle between the two step directions will be high. If high gradient values between the probability scores of the adjacent two-dimensional images are distributed in a small region along the set-direction, the direction of the current sequence will not deviate much from the set-direction of the previous sequence, i.e. the angle between the two set-directions will be small.

Figure 1:
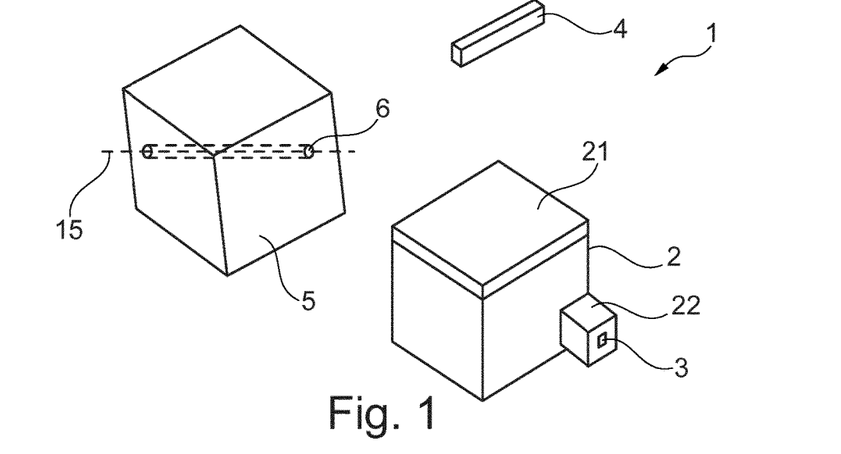
FIG. 1 shows a schematic view of an embodiment of the imaging system comprising the device for determining at least one final two-dimensional image.

FIG. 1 shows an imaging system 1. The imaging system 1 comprises an ultrasonic transducer 4 and a device 2 for determining at least one final two-dimensional image.

The ultrasonic transducer 4 is configured to image a body region of a patient via ultrasound waves. The ultrasonic transducer 4 provides a set of two-dimensional ultrasonic images of the body region. The images provided by the ultrasonic transducer 4 are converted by the system 1 to a three-dimensional image 5 of that body region. In that three-dimensional image 5 of a body region of the patient body an image of an applicator 6 may be shown.

The device 2 comprises an input interface 21 and a processing unit 22.

The output interface 21 is configured to receive the three-dimensional image 5 of a body region of a patient body. The three-dimensional image 5 may comprise an image of an applicator 6. The three-dimensional image may also be referred to a three-dimensional volume or a three-dimensional slice.

The processing unit 22 is configured to run a computer program element 3. The computer program element 3 may be configured to carry out the steps 104 to 107 of the method 100 described above.

Figure 2:
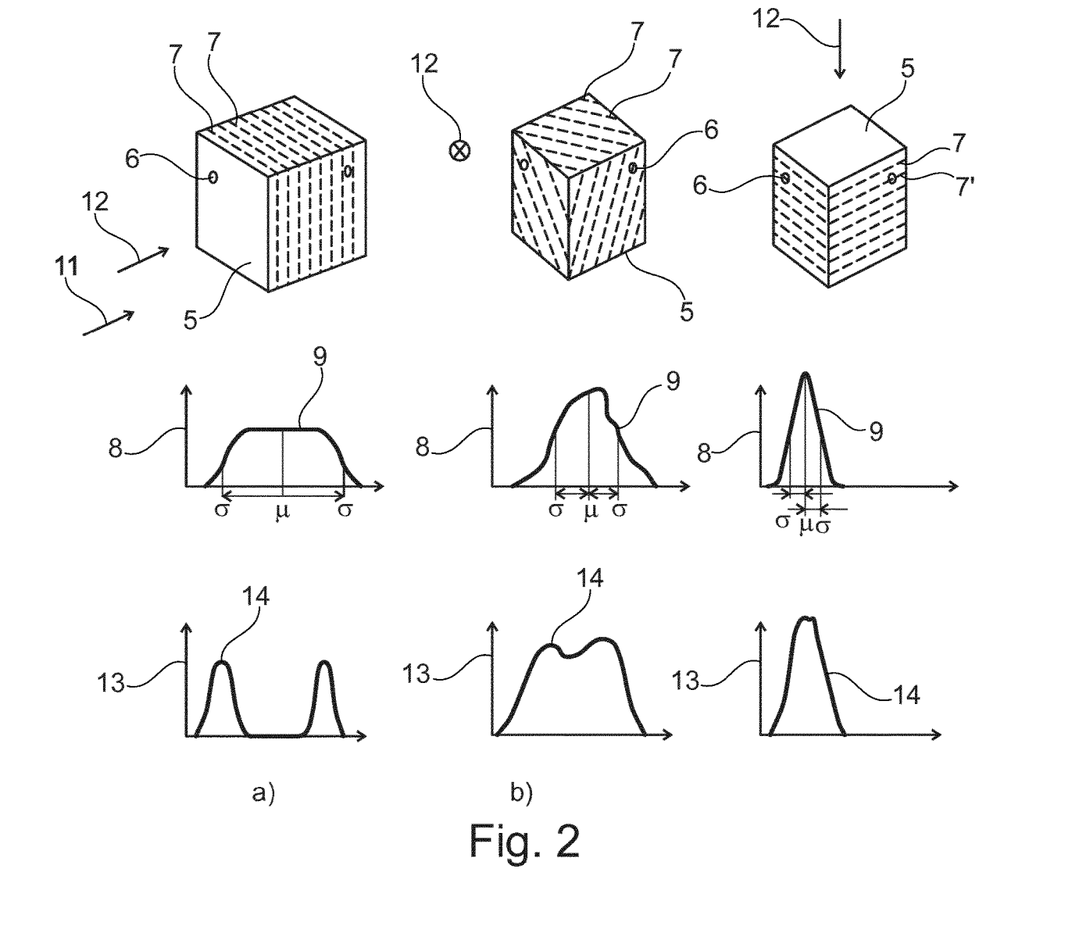
FIG. 2 shows a schematic view of an embodiment of the method steps concerning the slicing of the body region and the resulting probability map.

Referring to FIG. 2, in an example, the processing unit 22 is configured to randomly determine an initial direction 11 within the three-dimensional image 5.

In another example, the processing unit 22 receives a signal representing the initial direction 11 via the input interface 21. Thus, a user may input a desired initial direction 11 via the input interface 21.

In a further example, the processing unit 22 may access a predefined direction as the initial direction 11. The predefined direction may e.g. be stored in the processing unit 22 or at another location.

In a certain example, the processing unit 22 is configured to determine one of the predetermined Cartesian directions of the three-dimensional image as the initial direction 11.

Furthermore, the processing unit 22 is configured to determine a set-direction 12 within the three-dimensional image 5 based on the initial direction 11 for the first sequence or based on the probability map 8 determined during the previous sequence.

In an example, the above step may comprise the sub-steps of: Identifying the set-direction of the three-dimensional image through a statistical analysis on the probability map which fetches a compact representation of the applicator.

In an exemplary embodiment of the processing unit 22, the processing unit 22 comprises the sub-steps of determining the set-direction 12 which are performed only, if the set-direction 12 is to be determined based on the probability map 8 of at least one previous sequence.

First, the processing unit 22 determines the standard deviation σ based on the probability map 8.

Then, the processing unit 22 determines the set-direction 12 based on the standard deviation σ. If the standard deviation σ is high the set-direction 12 of the current sequence will deviate from the set-direction 12 of the previous sequence by a high amount, i.e. the angle between the set-direction 12 of the current sequence and the set-direction 12 of the previous sequence will be high. If the standard deviation σ is very low, the set-direction 12 of the current sequence will not deviate much from the set-direction 12 of the previous sequence, i.e. the angle between the set-direction 12 of the current sequence and the set-direction 12 of the previous sequence will be small.

As an effect, determining the set-direction 12 relates (except for the initial choice) to an iterative optimization algorithm.

In another exemplary embodiment of the processing unit 22, the processing unit 22 comprises alternative sub-steps which are performed only if the set-direction 12 is to be determined based on the probability map 8 of the previous sequence.

First, the processing unit 22 determines a gradient map 13 based on the probability map 8. This means that the gradient values 14 between the probability scores 9 of adjacent two-dimensional images 7 of the three-dimensional image 5 are determined. The gradient map 13 comprises the plurality of determined gradient values 14 and maps them to the position of the corresponding two-dimensional image 7 in the three-dimensional image 5.

In the next step, the processing unit 22 determines the set-direction 12 based on the gradient map 13. This means, if the distribution of high gradient values 14 cover a high amount of the two-dimensional images 7, i.e. covering an extended region along the set-direction 12, the set-direction 12 of the current sequence will deviate from the set-direction 12 of the previous sequence by a high amount, i.e. the angle between the two set-directions 12 of the current and previous sequence will be high. If the distribution of the gradient values 14 between the two-dimensional images 7 is low or is distributed in a small region along the set-direction 12, the set-direction 12 of the current sequence will not deviate much from the set-direction 12 of the previous sequence, i.e. the angle between the two set-directions 12 will be small.

Furthermore, the processing unit 22 extracts and image set of two-dimensional images 7 from the three-dimensional image 5, such that the two-dimensional images 7 of the image set are arranged coaxially and subsequently in the set-direction 12. In an example, the extraction by the processing unit 22 is performed such that the two-dimensional images 7 represent virtual slices of the body region.

As an effect, the correspondence between the images and the virtual slices is provided.

In an example, the processing unit 22 is configured to extract the image-set of two-dimensional images 7 such that the two-dimensional images 7 represent the three-dimensional image 5 in total.

As an effect, the three-dimensional image 5 is divided into the two-dimensional images 7 during the extraction of the two-dimensional images 7 of each sequence. Thus, for each evaluation of the respective probability scores 9, always the whole three-dimensional image 5 is indirectly considered via the two-dimensional images 7.

Then, the processing unit 22 applies an applicator pre-trained classification method to each of the two-dimensional images 7 of the image set indicating a probability of the applicator 6 being depicted in the respective two-dimensional image 7 of the image set in a cross-sectional view.

In an example, the applicator pre-trained classification method is an applicator pre-trained deep learning classification method.

In a further example, the applicator pre-trained classification method is an applicator pre-trained convolutional neuronal network classification method.

In a certain example, the applicator pre-trained classification method is pre-trained with a google net architecture or with a hyper-parameter fine-tuning Further, the processing unit 22 determines a probability map 8 representing probability scores 9 of the two-dimensional images 7 of the image set with respect to the set-direction 12. In an example, the processing unit 22 applies a Gaussian fit to the probability scores 9 of the two-dimensional images 7 of the image-set for determining the probability map 8.

As an effect, the probability will approximate a Gaussian curve representing the probability scores 9 about the set-direction 12 or the number of two-dimensional images 7, respectively.

In an example, the processing unit may repeat the above sequence several times. At each sequence, an improved set-direction 12 may be determined, along which a set of two-dimensional-images 7 are extracted from (the same) three-dimensional-image 5. The probability associated with each image may provide the information about a compactness of an indication of the applicator 6 within the respective two-dimensional-image 7. A probability may be determined based on the probabilities of the two-dimensional-image 7. At the next sequence, this probability map 8 may be considered, to determine a new set-direction 12. Thus, an optimization of the set-direction 12 may be achieved. As an effect, the images acquired along an optimized or best set-direction 12, respectively, may comprise at least one two-dimensional-image 7, which indicate a (very) compact representation of the applicator 6. Thus, the at least one image may illustrate a cross-sectional view of the full applicator 6.

In an exemplary embodiment, the processing unit 22 is configured to finish the repetition of the sequence, i.e. the repetition of the sequence, if a high probability score 9 of probability scores 8 of the two-dimensional images 7 of the current image set is higher than a predefined value. Alternatively, the processing unit 22 finishes the repetition of the sequences if one two-dimensional image 7 of the two-dimensional images 7 of the current image set entirely depicts the actuator 6 in a cross-sectional view. This means, that if a slice of the three-dimensional image 5 comprises the longitudinal axis 15 of the actuator 6 or is at least parallel to the longitudinal axis 15 of the actuator 6 and comprises a cross-sectional view of the actuator 6 the sequence is finished. Alternatively, if the angle between the longitudinal axis 15 and the slice of the three-dimensional image 5 is below a certain threshold such that the probability score 9 of one of the slices exceeds a predefined threshold value, the sequence will be finished, too.

In an example, the predefined value may be chosen or predefined, such that it can be assumed that the two-dimensional image 7 corresponding to the respective highest value at least almost entirely depicts the actuator 6 in a cross-sectional view.

In a further embodiment of the processing unit 22, the processing unit 22 determines a standard deviation σ based on the probability map 8 of the current sequence. This means, that the maximum value of the probability scores 9 of a probability map 8 of the current sequence is determined. Then, the standard deviation σ of the plurality of probability scores 9 from that maximum value is determined.

Then, the processing unit 22 stops the repetition of the sequences if determined standard deviation σ represents a minimum standard deviation σ about all determined standard deviation σ. The determined standard deviation σ of the current sequence is therefore compared to the determined standard deviation σ of the previous sequences. If one of the previous sequences comprises the minimum standard deviation σ about all sequences, i.e. if the standard deviation σ of the current sequence is higher than one of the previous sequences, the repetition of the sequence is stopped.

As an effect, the value of the standard deviation σ may provide the basis for a stopping criteria of the repetition of the sequence.

After finishing the last sequence, the processing unit 22 determines the two-dimensional image 7 associated with the highest probability score 9 as the final two-dimensional image. The final two-dimensional image may be formed by the two-dimensional image 7 associated with the highest probability score 9.

In an example, the final two-dimensional images is formed by the two-dimensional image 7 associated with the highest probability score 9 from the image set determined during the last sequence.

In an example, the probability may represent a Gaussian probability map, wherein the standard deviation σ decreases from sequence to sequence. Thus, the probability map 8 determined during the last sequence may comprise the two-dimensional-image 7 for which the highest probability score 9 is determined.

In an example, determining the set-direction 12 based on the probability may relate to an application of an iterative optimization algorithm, in particular a gradient descent algorithm.

FIG. 2 further exemplary shows sequences a), b) and c) of the starting and repeated sequence. Sequence a) is the starting sequence. The initial direction 11 being determined by the processing unit 22 is used to determine the set-direction 12.

Then, the three-dimensional image 5 of the body region of the patient, wherein the three-dimensional image 5 comprises an image of the applicator 6, is virtually sliced. The slicing is performed along the set-direction 12 and results in a set of two-dimensional images 7. The slicing planes are parallel and may be equidistant.

In sequence a), all determined two-dimensional images 7 comprise a small cross section of the image of the applicator 6. Therefore, the applicator pre-trained classification method provides a low probability score 9 to each of the two-dimensional images 7. This is shown in the probability map 9 of sequence a).

In sequence b) the set-direction 12 is chosen such that the angle between the set-directions 12 of sequences a) and b) is big. The set-direction 12 of sequence b) points into the plane of FIG. 2.

The two-dimensional images 7 acquired in sequence b) do not all comprise an image of the cross section of the applicator 6. The applicator pre-trained classification method therefore assigns a low probability score 9 to those two-dimensional images 7 which do not comprise any cross-sectional view of the applicator 6. Those two-dimensional images 7 of sequence b) comprising a portion of the cross-sectional view of the applicator 6 get a higher probability score 9 than the two-dimensional images 7 of sequence a).

The resulting probability map 8 of sequence b) shows a tighter distribution of the probability scores 9 than in the probability map 8 of sequence a).

Sequence c) shows a later sequence, i.e. between sequence b) and sequence c) a plurality of repeated sequences may have been performed. The set-direction 12 of sequence c) has been determined by the process steps. In sequence c) only a single two-dimensional image 7' comprises a cross-sectional view of the applicator 6. The rest of the two-dimensional images 7 does not comprise any portion of the image of the applicator 6.

Therefore, the probability map 8 of sequence c) shows a peak of the probability scores 9 at the position of the single two-dimensional image 7'. The probability score 9 at the peak is very high. The rest of the probability scores is low since the corresponding two-dimensional images 7 do not comprise any portion of the image of the applicator 6.

The single two-dimensional image 7' may be chosen to form the finial two-dimensional image being presented to the user.

In an example, the system 1 is configured such that a two-dimensional image 7 is taken over from one of the plurality of the two-dimensional ultrasonic images, if the overtaken two-dimensional ultrasonic image fits into the respective image-set.

As an effect, interpolation artefacts may be prevented or reduced.

Moreover, although in the previous description the word "device" has been used, whenever the word "device" is mentioned it is understood that this might indeed refer to a full device but also to just a fraction of a device.

It is understood that, without repeating here all the examples and explanations provided with reference to the method of the invention, the apparatus and system of the invention are intended as being arranged to carry out the above described method steps. Thus, all the above examples and explanations, although provided with reference to the method, are also to be intended as being implemented by the apparatus and/or the system. This can be achieved, for example, by means of suitable hardware and/or software.

It is understood that, without repeating here all the explanations, examples, features and/or advantages provided with reference to the device, the method of the invention is intended to be configured to carry out the method steps for which the device is configured to. Thus, all the above examples, explanations, features and/or advantages, although provided with reference to the device, are also to be intended as being provided in an analogous manner for the method.

According to a further example of the present invention, a computer program element 3 is provided, which, when being executed by a processing unit is adapted to carry out the method 100 described above.

Figure 6:
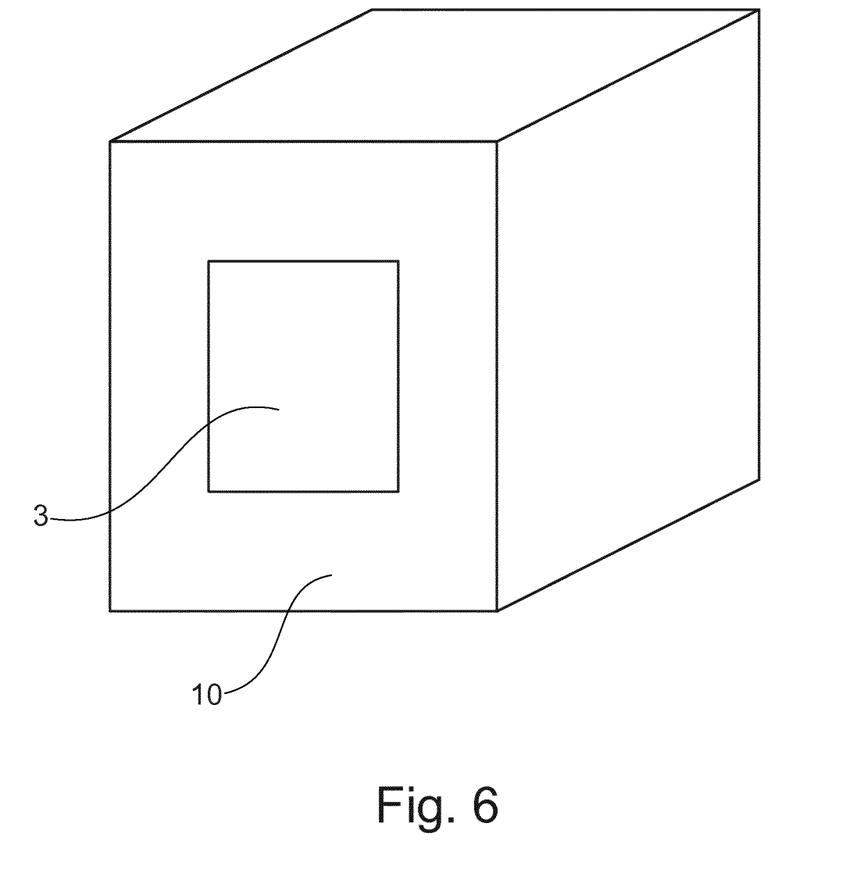
FIG. 6 shows a schematic view of an embodiment of a computer readable medium.

According to further example of the present invention, a computer readable medium 10 being shown in FIG. 6, the computer readable medium having stored thereon a program element 3 is provided, which, when being executed by a processing unit is adapted to carry out the method 100 described above.

The computer program element 3 might be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

It should be noted that embodiments of the invention are described with reference to different subject matters. In particular, some embodiments are described with reference to an insert whereas other embodiments are described with reference to the apparatus. However, a person skilled in the art will gather from the above that, unless otherwise notified, in addition to any combination of features belonging to one subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for determining at least one final two-dimensional image, wherein the device comprises:
   an input interface;
   a processing unit;
   wherein the input interface is configured to receive a three-dimensional image of a body region of a patient body, wherein an object of interest is located in the body region;
   wherein the processing unit is configured to randomly determine an initial direction within the three-dimensional image, to receive a signal representing the initial direction via the input interface or to access a predefined direction as the initial direction;
   wherein the processing unit is configured to repeat the following sequence of steps s1) to s4):
   s1) to determine a set-direction within the three-dimensional image based on the initial direction for the first sequence or based on a probability map determined during a previous sequence;

s2) to extract an image-set of two-dimensional images from the three-dimensional image, such that the two-dimensional images of the image-set are arranged coaxially and subsequently in the set-direction;

s3) to apply an object of interest pre-trained classification method to each of the two-dimensional images of the image-set resulting in a probability score for each of the two-dimensional images of the image-set indicating a probability of the object of interest being depicted, in particular fully depicted, in the respective two-dimensional image of the image-set in a cross-sectional view; and s4) to determine a probability-map representing the probability scores of the two-dimensional images of the image-set with respect to the set-direction;

wherein the processing unit is configured to determine, after finishing the last sequence, the two-dimensional image associated with the highest probability score, in particular from the image-set determined during the last sequence, as the final two-dimensional image.

2. The device according to claim 1, wherein the final two-dimensional image is formed by the two-dimensional image associated with the highest probability score, in particular from the image-set determined during the last sequence.

3. The device according to claim 1, wherein the processing unit is configured to perform step s2) such that the two-dimensional images of the image-set represent virtual slices of the body region.

4. The device according to claim 1, wherein the processing unit is configured to apply a Gaussian fit to the probability scores of the two-dimensional images of the image-set for determining the probability map.

5. The device according to claim 1, wherein the processing unit is configured to perform step s4) with a sub-step:
s4.1) to finishing the repetition of the sequence,
if the highest probability score of the probability scores of the two-dimensional images of the current image-set is higher than a predefined value, or
if one two-dimensional image of the of the two-dimensional images of the current image-set entirely depicts the object of interest in a cross-sectional view.

6. The device according to claim 1, wherein the processing unit is configured to perform step s4) with sub-steps:
s4.2) to determine a standard deviation a based on the probability map determined during the current sequence; and
s4.3) to finish the repetition of the sequence, if a standard deviation σ
determined during the at least one previous sequence represents a minimum standard deviation about all determined standard deviation σ.

7. The device according to claim 1, wherein the processing unit is configured to perform step s1), if the set-direction is to be determined based on the probability map, with the following sub-steps:
s1.1) to determine a standard deviation a based on the probability map; and
s1.2) to determine the set-direction based on the standard deviation σ.

8. The device according to claim 1, wherein the processing unit is configured to perform step s1), if the set-direction is to be determined based on the probability map, with the following sub-steps:
s1.1) to determine a gradient map based on the probability map; and
s1.2) to determine the set-direction based on the gradient map.

9. The device according to claim 1, wherein the processing unit is configured to provide the item of interest pre-trained classification method as an item of interest pre-trained deep learning classification method.

10. The device according to claim 1, wherein the item of interest pre-trained classification method is an applicator pre-trained convolutional neuronal network classification method.

11. The device according to claim 1, wherein An imaging system for determining at least one final two-dimensional image of a body region of a patient body, wherein an object of interest is located in the body region, wherein the system comprises:
an ultrasonic transducer; and
wherein the ultrasonic transducer is configured to acquire a plurality of two-dimensional ultrasonic images of the body region; and
wherein the system is configured to determine a three-dimensional image of the body region based on the plurality of two-dimensional ultrasonic images.

12. The imaging system according to claim 11, wherein the processing is configured to perform step s2), such that a two-dimensional image is taken over from one of the plurality of the two-dimensional ultrasonic images, if the overtaken two-dimensional ultrasonic image fits into the respective image-set.

13. The device according to claim 1, wherein the object of interest is a medical instrument inserted into the body region.

14. A method for determining at least one final two-dimensional image, the method comprises the steps:
a) providing a three-dimensional image of a body region of a patient body, wherein an object of interest is located in the body region;
b) providing an initial direction;
c) repeating the following sequence of steps s1) to s4):
s1) determining, via a processing unit, a set-direction within the three-dimensional image based on the initial direction for the first sequence or based on a probability map determined during a previous sequence;
s2) extracting, via the processing unit, an image-set of two-dimensional images from the three-dimensional image, such that the two-dimensional images of the image-set are arranged coaxially and subsequently in the set-direction;
s3) applying, via the processing unit, an applicator pre-trained classification method to each of the two-dimensional images of the image-set resulting in a probability score for each of the two-dimensional images of the image-set indicating a probability of the applicator being depicted, in particular fully depicted, in the respective two-dimensional image of the image-set in a cross-sectional view; and
s4) determining, via the processing unit, a probability-map representing the probability scores of the two-dimensional images of the image-set with respect to the set-direction;
wherein the method comprises the further step:
d) determining, via a processing unit and after finishing the last sequence, the two-dimensional image associated with the highest probability score, in particular from the image-set determined during the last sequence, as the final two-dimensional image.

15. A computer program element stored on a non-transitory computer-readable medium, for controlling a device, that includes
an input interface; and
a processing unit;

wherein the input interface is configured to receive a three-dimensional image of a body region of a patient body, wherein an object of interest is located in the body region;

wherein the processing unit is configured to randomly determine an initial direction within the three-dimensional image, to receive a signal representing the initial direction via the input interface or to access a pre-defined direction as the initial direction;

wherein the processing unit is configured to repeat the following sequence of steps s1) to s4):

s1) to determine a set-direction within the three-dimensional image based on the initial direction for the first sequence or based on a probability map determined during a previous sequence;

s2) to extract an image-set of two-dimensional images from the three-dimensional image, such that the two-dimensional images of the image-set are arranged coaxially and subsequently in the set-direction;

s3) to apply an object of interest pre-trained classification method to each of the two-dimensional images of the image-set resulting in a probability score for each of the two-dimensional images of the image-set indicating a probability of the object of interest being depicted, in particular fully depicted, in the respective two-dimensional image of the image-set in a cross-sectional view; and s4) to determine a probability-map representing the probability scores of the two-dimensional images of the image-set with respect to the set-direction;

wherein the processing unit is configured to determine, after finishing the last sequence, the two-dimensional image associated with the highest probability score, in particular from the image-set determined during the last sequence, as the final two-dimensional image.

16. The method of claim 15, wherein the initial directed is provided by randomly determining the initial direction within the three-dimensional image.

* * * * *